United States Patent [19]

Burrows

[11] 4,184,445
[45] Jan. 22, 1980

[54] SOIL MOISTURE SIGNALING DEVICE

[75] Inventor: Walter H. Burrows, Atlanta, Ga.

[73] Assignee: Compac Industries, Inc., Atlanta, Ga.

[21] Appl. No.: 869,470

[22] Filed: Jan. 16, 1978

[51] Int. Cl.² ................... G01N 31/06; G01N 31/22
[52] U.S. Cl. .................................... 116/206; 73/73
[58] Field of Search ....... 116/114 AM, 118 A, 114 R, 116/206; 73/73; 206/820

[56] References Cited

U.S. PATENT DOCUMENTS

| | | | |
|---|---|---|---|
| 2,627,505 | 2/1953 | Goodwin | 252/408 |
| 2,929,241 | 3/1960 | Gebhart | 73/73 |
| 2,951,461 | 9/1960 | Lockwood | 116/114 AM |
| 3,019,638 | 2/1962 | Klein | 73/73 |
| 3,144,343 | 8/1964 | Fritsche | 206/820 |
| 3,824,844 | 7/1974 | Strickland | 73/73 |
| 3,951,098 | 4/1976 | Meyers | 116/114 AM |

Primary Examiner—S. Clement Swisher
Assistant Examiner—Denis E. Corr
Attorney, Agent, or Firm—Jones, Thomas & Askew

[57] ABSTRACT

This invention relates to a device that may be inserted into the soil of a potted plant for the purpose of determining the soil moisture content thereof. The device employs a moisture sensitive signalling element and a tube-shaped humidity chamber which provides means for establishing an equilibrium condition between the moisture content of the soil and the moisture content of the air surrounding the signalling element, thereby providing an accurate indicator of soil moisture content.

1 Claim, 5 Drawing Figures

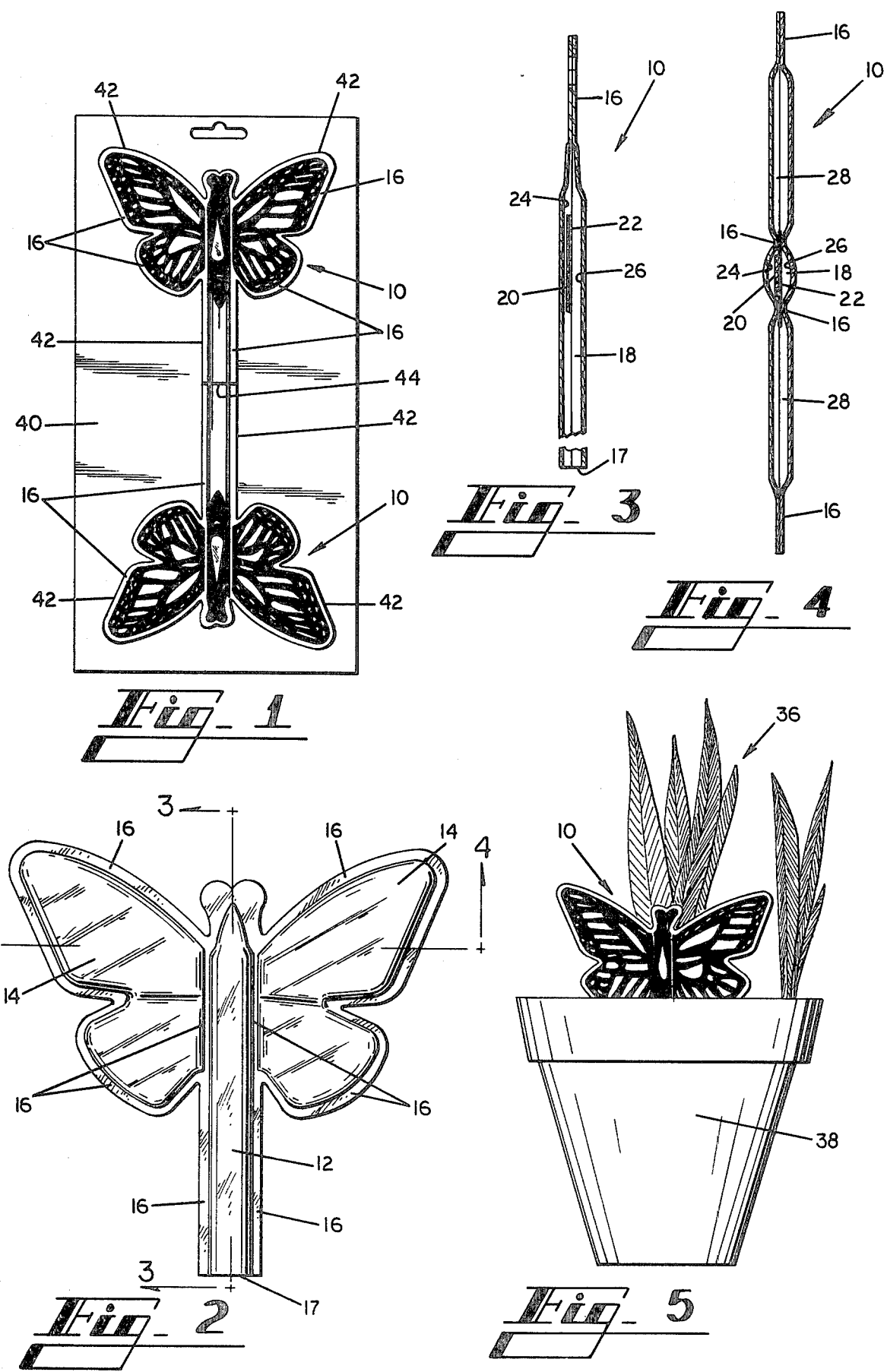

SOIL MOISTURE SIGNALING DEVICE

With the recent surge in interest and popularity in house flora, a number of devices have been developed to monitor the moisture content of potting soil so that the owner will neither overwater or underwater the plant. However, these previously known devices all suffer from defects which make a true indication of soil moisture content either improbable, unreliable or accidential.

Devices capable of giving accurate representation of soil moisture are usually too complex or too costly for the amateur horticulturist. The inexpensive variety of moisture monitoring devices use an absorbent material to act as a wick to transport the moisture from below soil level up to the signalling device which is easily visible above the soil surface. See Meyers U.S. Pat. No. 3,951,098, Strickland U.S. Pat. No. 3,824,844 and Klein U.S. Pat. No. 3,019,638. It is this wick concept that inherently induces error into previous soil moisture indicators.

Strickland utilizes a tissue paper wick sealed between two layers of plastic. However, since the wick is isolated from the atmosphere around it, it will retain water long after the soil dries out.

In an attempt to remedy this disadvantage, Meyers provided holes punched through the plastic housing and wick so as to dispel the excess moisture through these venting openings. However, if the wick is not in contact with the moisture in the soil at all times, this venting may dry the wick excessively, causing an erroneous reading. This error is presumably circumvented by means of holes punched through the wick and housing below the soil line. Unfortunately, these holes provide means for liquid water to enter, flooding the bottom of the wick and remaining there to keep the wick moist long after surrounding soil has dried.

Accordingly, it is an object of the present invention to provide a device which can provide an accurate indication of soil moisture content.

It is a further object of this invention to provide a method of producing said soil moisture indicator in a manner such that it is attached to a card suitable for display purposes.

A further object of this invention is to provide a method of producing two soil moisture indicating devices from the same pieces of material.

It is yet another object of this invention to provide a soil moisture indicator that is attractive and inexpensive to produce.

Other objects and advantages of this invention will be apparent from the following detailed description, the accompanying drawings and the appended claims.

DESCRIPTION OF THE DRAWING

FIG. 1 is a plan view of the device of the invention still attached to its display card.

FIG. 2 is a plan view of the device of the invention.

FIG. 3 is a cross-sectional view taken along lines 3—3 of FIG. 2 of the indicator. The tube is shown broken into sections to reduce its length for simplicity of display.

FIG. 4 is a cross-sectional view taken along lines 4—4 of FIG. 2 of the indicator.

FIG. 5 is a pictorial view of the device of the invention as it would be used with a typical potted houseplant.

DETAILED DESCRIPTION OF THE DRAWINGS

Referring to FIG. 2 it will be seen that the soil moisture indicator 10 of the present invention is composed of an elongate sampling tube 12 of a generally circular cross-sectional shape and butterfly wings 14. Sampling tube 12 is composed of a front and a back layer of molded transparent plastic material. The front and back layers of plastic have been sealed together by appropriate means, such as heat sealing or adhesives, around the periphery 16 of sampling tube 12 and butterfly wings 14. Three hollow chambers are thereby provided in those spaces where the front and back layers of plastics have not been sealed together.

Referring now to FIGS. 2, 3 and 4 it will be seen that the upper end of sampling tube 12 is closed while the lower end is open. The opening in the lower end of sampling tube 12 provides an entrance 17 to humidity chamber 18. The humidity chamber 18 is the hollow chamber defined by the front and back layers of plastic and surrounded by the sealed edge which constitutes the periphery 16 of the sampling tube 12.

The humidity chamber 18 has an upper portion and a lower portion, with the upper portion being that section of the humidity chamber which is adjacent but sealed from the butterfly wings 14. Suspended within the upper portion of humidity chamber 18 is color indicator tab 20. The color indicator tab 20 may be any suitable absorbent material, such as white filter paper, which has been treated so as to produce a change in color depending on the humidity of the air surrounding it. Various cobalt compounds are known in the art to produce the desired color changes.

The color indicator tab 20 is attached to support film 22 which is a thin transparent plastic film traversing the entire width of the humidity chamber 18 and attached at each end to the sealed edge of the periphery 16 of the upper portion of the humidity chamber. Suspending the color indicator tab 20 within humidity chamber 18 in this manner prevents the absorbent material of the indicator tab from actually contacting the inner walls 24 and 26 of sampling tube 12. This provides an added advantage in that if condensation of moisture forms on the inner walls 24 and 26 of sampling tube 12, leeching of the moisture sensitive chemicals from the color indicator tab 20 will be prevented. It has been found that this arrangement provides a moisture signalling element that has a life expectancy of at least 200 cycles, corresponding to approximately one year of service, whereas the devices of the prior art have a life expectancy of only 90 days. This arrangement also prevents artificial and long term color changes resulting from condensation which produce erroneous indications in prior art devices.

It will be seen that the upper portion of the humidity chamber 18 which contains the color indicator tab 20 does not include the volume contained in the butterfly wings chambers 28. The humidity chamber 18 is isolated from the butterfly wings chambers 28 by the sealed edges of the plastic material which constitutes the periphery 16 of the humidity chamber 18. The raised butterfly design and the butterfly wing chambers 28 serve no functional purpose to the operation of the invention. The inclusion of this raised design is merely to enhance the aesthetic appeal of the invention. The invention contemplates the use of other appealing designs, such as flowers and the like, for that portion of the device outside of the humidity chamber and sampling tube which are the essential functional portions of the invention.

The overall size of the soil moisture indicator may be changed to match larger or smaller pots, plants, or surroundings. However, the inner diameter of humidity chamber 18 should provide an interior cross-sectional area of not less than about one square centimeter. Further, the distance from the entrance 17 of humidity chamber 18 to the color indicator tab 20 should be proportionately related to the interior cross-sectional area of humidity chamber 18. That is, if the cross-sectional area is one square centimeter, the distance from the entrance 17 of humidity chamber 18 to color indicator tab 20 should be from 4 to 6 centimeters, preferably 5 centimeters. This ratio of 1:4 to 1:6 is a critical feature of the invention and should be maintained for all variations in size of the soil moisture indicator.

FIG. 5 shows a typical house plant 36 planted in a pot 38 containing soil in which the soil moisture indicator 10 is implanted. To implant the device a hole is made in the soil adjacent the rooted plant 36. The depth of the hole should coincide with the anticipated level of moisture in the soil. For dry soils that drain rapidly, the device should penetrate about 1½ inches below the soil's surface. For soils that retain moisture for a long time, ½ inch is preferable. The lower portion of sampling tube 12 of the device is then placed in the hole in the soil. Excess dirt may then be filled in around the tube. Care should be taken to avoid pushing the sampling tube into the soil because dirt may then clog humidity chamber 18. It is an essential aspect of this invention that an air space be provided in humidity chamber 18 between the area of color indicator tab 20 and the surface of the soil to be monitored at the desired level of monitoring within the soil.

In operation, moisture from the soil will evaporate into the air contained in humidity chamber 18. Since humidity chamber 18 is sealed at the end projecting out of the soil, the moisture in the vapor phase contained in humidity chamber 18 will not escape to the atmosphere, but rather merely permeate the air contained in the chamber. An equilibrium condition is therefore automatically established between the liquid phase of the moisture contained in the soil and the vapor phase of the moisture in the air in the humidity chamber 18. Any change in moisture content of the soil will automatically be reflected in a corresponding change in the moisture content of the air in humidity chamber 18.

The color indicator tab 20 is located in the upper portion of humidity chamber 18. As moisture vapor enters humidity chamber 18 it fills the chamber surrounding the color indicator tab. The color indicator tab 20, which has been treated with a moisture sensitive chemical, reacts to the change in humidity. At a certain humidity a "color break" results in the color indicator tab. When using a cobalt compound as the moisture sensitive chemical, as the humidity approaches this "color break" point, the color of the color indicator tab, which is initially blue under dry conditions, changes to a pale pink or almost white. Thus, when the plant is freshly watered the color indicator tab will show light pink. As moisture is withdrawn from the soil by evaporation and transpiration, the moisture in humidity chamber 18 will decrease producing a change in the color of the color indicator tab to blue. Thus, it will be seen that the color change of the color indicator tab 20 accurately reflects the moisture condition of the soil in which sampling tube 12 is buried at the level of the soil at the bottom of the tube.

The color indicator tab 20 may be prepared in the following manner: a solution of cobaltous thiocyanate suitable for the impregnation of the absorbent material is prepared by reacting equal volumes of (a) a solution containing 1 mole per liter of a suitable cobalt salt, such as the acetate, bromide, fluoride, iodide, nitrate, perchlorate or sulfate, and (b) a solution containing 4 moles per liter of ammonium thiocyanate. The resulting solution is 0.5 molar with respect to cobaltous thiocyanate and its color is blue. This solution is then diluted with water until it becomes pink. Approximately one volume of water is required for each volume of the solution. Additional water may be added as needed, depending upon the intensity of color desired in the treated media. A small quantity of a suitable humectant such as glycerin or propylene glycol may be added to adjust the solution to the desired humidity color break. The use of an humectant is optional. Cobalt compositions having color break points at predetermined relative humidities are well known in the art and are described, for example, in U.S. Pat. No. 2,627,505, the disclosure of which is incorporated by reference herein. A suitable color break for the color indicator tab of this invention is a relative humidity of approximately 75%. The absorbent material to be used for the color indicator tab is then dipped into the treating solution and permitted to drain and dry either at ambient or elevated temperatures.

Referring now to FIG. 1, two soil moisture indicators 10 are mounted end-to-end on a display card 40. The display card 40 and the soil moisture indicators 10 are composed of a front and back layer of molded transparent plastic material. The layers of molded plastic are identical in construction and by placing two identical layers together, one pair of indicators 10 and associated display card are produced. When the front layer and back layer are then sealed together the resulting product is a display card with the soil moisture indicator mounted therein. Various known molding and sealing techniques, such as vacuum forming and heat sealing, may be used. Before lamination, the underside of each plastic sheet may be printed with various types of instructional information or color designs so as to render the final product more attractive. Perforations are provided in both layers of plastic around the outer edge 42 of the periphery 16 of the soil moisture indicator so that the indicator may be easily separated from the display card. After the soil moisture indicators 10 have been separated from display card 40 each indicator is prepared for use by cutting along bisection line 44. The entrance 17 to humidity chamber 18 is thereby provided by the bisection line 44 which also separates the indicators from each other so as to be ready for use.

Any transparent or translucent material which permits construction of the device as disclosed herein, and which will withstand deterioration from the elements and is of sufficient thickness to have the necessary mechanical strength is satisfactory for use in constructing the soil moisture indicator. Suitable materials include resins of polyvinyl chloride, polyethylene, polypropylene, polyethylene terephthalate, "Mylar", glass, metal, acrylonitrile-butadiene-styrene, cellulose acetate, cellulose triacetate, cellulose acetate butyrate, cellulose propionate, ethyl cellulose, cellophane, ionomer, polymethyl methacrylate, polycarbonate, nylon, ethylene vinyl acetate copolymer, polyimide, polystyrene, vinyl acetate-chloride copolymer, and the like.

It should be understood that the previously described embodiment merely illustrates principles of the invention in selected, preferred form. Many modifications, additions and deletions, of course, may be made thereto without departing from the spirit and scope of the invention as set forth in the following claims.

What is claimed is:

1. A soil moisture indicating device together with a display card comprising:

two sheets of plastic material having contacting surface areas and non-contacting surface areas, wherein said contacting surface areas of the two sheets are joined together over the majority of the entire surface of said two sheets and which comprise said display card, and said non-contacting surface area defines a hollow tube-shaped chamber;

a boundary between said contacting surface area and said non-contacting surface area, with said boundary being perforated so as to facilitate separation of said hollow tube-shaped chamber from said display card;

a moisture sensitive, color changeable signal element mounted in each end of said hollow tube-shaped chamber; and a bisection line located at the mid-point of the length of said hollow tube-shaped chamber.

* * * * *